United States Patent [19]

Burkhart

[11] Patent Number: 5,044,363

[45] Date of Patent: Sep. 3, 1991

[54] ADSORPTION SYSTEM FOR SCAVENGING ANESTHETIC AGENTS FROM WASTE GAS RELEASED DURING SURGICAL ACTIVITY

[75] Inventor: Joseph E. Burkhart, Morgantown, W. Va.

[73] Assignee: The United States of America as represented by the Department of Health and Human services, Washington, D.C.

[21] Appl. No.: 528,080

[22] Filed: May 24, 1990

[51] Int. Cl.$^5$ .............................................. A61M 16/10
[52] U.S. Cl. ........................... 128/205.27; 128/204.18; 128/201.25; 128/203.12; 128/205.12; 128/910
[58] Field of Search ....................... 128/204.18, 201.25, 128/910, 203.12, 205.12, 205.27

[56] References Cited

U.S. PATENT DOCUMENTS

| | | | |
|---|---|---|---|
| 1,175,006 | 3/1916 | Montgomery | 128/204.18 |
| 2,667,397 | 1/1959 | Hallisey | 128/204.18 X |
| 3,791,403 | 2/1974 | Folkerth | 128/204.18 X |
| 3,867,936 | 2/1975 | Kelley | 128/910 X |
| 3,941,573 | 5/1976 | Chapel | 55/316 |
| 4,026,284 | 5/1977 | Boehringer | 128/910 X |
| 4,082,092 | 4/1978 | Foster | 128/910 X |
| 4,109,651 | 8/1978 | Steigerwald | 128/910 X |
| 4,188,946 | 2/1980 | Watson et al. | 128/910 X |
| 4,259,303 | 3/1981 | Nakaji et al. | 128/910 X |
| 4,382,440 | 5/1983 | Kapp et al. | 128/201.25 |

FOREIGN PATENT DOCUMENTS 3219444  3/1983  Fed. Rep. of Germany ........................ 128/203.12

OTHER PUBLICATIONS

A. M. Bickford Inc. brochure titled "Anesthesia Gas Filter unit, OMNICON F/AIR", Wales Center, N.Y.

Primary Examiner—Edgar S. Burr
Assistant Examiner—E. P. Raciti
Attorney, Agent, or Firm—Lowe, Price, LeBlanc and Becker

[57] ABSTRACT

A cartridge loosely containing powdered activated charcoal is connected to a conventional anesthetic administration system of the type commonly used in veterinary surgical facilities. The cartridge is readily supported by a conventional anesthetic cart and is usable in both rebreathing and pass-through operation of the anesthetic-administration system. Gases of vaporized anesthetic substances that typically are released from the pop-off valve of liquid anesthetic containers or in the exhalations from the animal patient are both selectively directed through the activated charcoal without the need for motors, blowers, or other devices requiring power. The invention utilizes commonly available materials such as PVC pipe and end fittings, powdered activated charcoal and fiberglass filter elements, and assorted commercially available pipe fittings. In relatively compact form, this invention enables the removal of approximately 95% of anesthetic substances that otherwise would be released where they would likely be breathed in by and do harm to surgery personnel. The cartridge may be shaken to rearrange the particles of activated charcoal, to thereby generate new gas-flow paths between newly-exposed surfaces that can adsorb more anesthetic substances.

13 Claims, 3 Drawing Sheets

ADSORPTION SYSTEM FOR SCAVENGING ANESTHETIC AGENTS FROM WASTE GAS RELEASED DURING SURGICAL ACTIVITY

TECHNICAL FIELD

This invention relates to preventing release of gases or vaporized anesthetic substances into the ambient atmosphere in facilities where such substances are used.

BACKGROUND ART

Veterinary clinics are typically small businesses without access to air scavenging systems of the type found in large clinics or hospitals. Surgical operations and pre-surgical preparations routinely require the use of anesthetic substances in gaseous or vaporized form. Human exposure to commonly used anesthetic substances such as halothane, methoxyflurane or isoflurane has been linked to a myriad of health-related problems. Unless great care is exercised, undesirable levels of exposure to such anesthetic substances is possible, particularly in small clinics, because many of them use portable anesthetic delivery carts which are not provided with devices to capture waste gases.

In this context, the term "waste gases" should be understood to comprehend potentially harmful gaseous substances such as those listed above, whether these are released with the exhalations from the animal patient or due to venting from anesthetic supply containers.

In relatively large facilities there is often provision for adequate ventilation, and scavenging means are disposed to ensure that potentially harmful substances are promptly removed from the breathing zones immediately adjacent surgeons and their staff. This may be accomplished by providing flexible ducting to apply local suction, the purged air being released at a distance, e.g., outside the building where anesthetics are used in surgical activity. Such systems necessarily include fans driven by electric motors, i.e., they need power supplies and means for positively applying a suction to induce a flow to remove contaminated air. Such systems are therefore relatively expensive to purchase and install and require sophisticated maintenance to ensure efficient performance.

Reported estimates show that over 50,000 U.S. veterinarians, their technicians and assistants are routinely exposed to waste anesthetic agents. Chronic exposures to these agents have been linked to liver and kidney diseases, CNS effects, spontaneous abortions in females, congenital abnormalities and even cancer. See, for example, NIOSH: Criteria for a Recommended Standard—Occupational Exposure to Waste Anesthetic Gases and Vapors. DHEW(NIOSH) Pub. No. 77-140(1977).

In 1977, NIOSH published its criteria for limits on exposure to waste anesthetic agents, limiting exposure to $N_2O$ at less than 25 ppm and halogenated agents at 2 ppm during administration of anesthetics to patients. If a halogenated agent is used in conjunction with $N_2O$, then the recommended exposure limit is 0.5 ppm for the halogenated agent. The American Conference of Governmental Industrial Hygienists (ACGIH) has recently adopted 50 ppm as its 8-hour Threshold Limit Value/Time-Weighted Average (TLV/TWA) for exposures to halothane and 75 ppm (TLV/TWA) to enflurane, two commonly used anesthetic agents. See, for example, American Conference of Governmental Industrial Hygienists: Threshold Limit Values and Biological Exposure Indices for 1988–1989. Cincinnati, Ohio (1988). The TLV for halothane is based on medical, environmental and epidemiological data collected for occupational exposure to trichloroethylene. The TLV for enflurane is based on the assumption that it is a safer anesthetic agent than halothane, and that no adverse effects are known at subanesthetic concentrations. See, for example, American Conference of Governmental Industrial Hygienists: Documentation of Threshold Limit Values and Biological Exposure Indices, 5th ed. (1986). No ACGIH threshold limit value currently exists for exposures to methoxyflurane. Also, at present, no OSHA permissible exposure level (PEL) exists for exposure to anesthetic agents; nor do specific recommendations exist for scavenging systems suitable for use in veterinary clinics.

An experimental study was conducted in which waste anesthetic gas exposures were determined, using a modified Miran 1A infrared spectrometer at five veterinary clinics operating within a Morgantown, W.V., facility. This device was slightly modified for these tests to increase the intrument's response time. Time-Weighted average exposures for unscavenged systems using methoxyflurane and halothane ranged from 0.5 to 45.5 ppm and 0.2 to 105.4 ppm, respectively. The purpose of this study was to evaluate "typical" exposure situations and to thereby develop procedures for control methods and parameters deemed effective and practical in reducing exposure levels to acceptable limits. The present invention, in partial reliance on this and other comparable studies, is intended to address such needs.

Scavenging systems have generally been the most recommended and widely proven method of reducing anesthetic gas exposures. A typical scavenging system consists of a hose attached to the pop-off valve of a cart carrying oxygen and anesthetic containers, the hose venting to a return air system or to the outside environment through a hole in the wall of the structure of the clinic. Such systems can cost between $200.00 and $500.00 to purchase and install, which may be prohibitive to small veterinary clinics. The overall effectiveness of such systems in such environments has not yet been fully established. A major problem in using such known technology is that its effectiveness is usually a function of the length of the hose by which local suction is applied or venting accomplished.

If anesthesia is being administered in only one location, then hose scavenging probably would be the control method of choice. Experience shows, however, that anesthesia is often given and maintained at many locations other than just the operating room. In practice, anesthesia is normally given during prepping and scrubbing, which in most cases lasts longer than the actual surgery time. It is also not uncommon to see more than one anesthetic gas cart being used at the same time in areas other than the operating room, e.g., a patient examination room. In summary, a single-location hose scavenging system may not be practical and, usually, the layout of the clinic may not allow multiple systems to be installed at affordable cost.

There is, therefore, a need for a compact, inexpensive, efficient and easy-to-maintain system mountable to individual anesthetic gas carts for removing ambient anesthetic substances from locations where humans would otherwise suffer repeated and unacceptably high levels of exposure to such substances.

DISCLOSURE OF THE INVENTION

Accordingly, it is a principal object of this invention to provide a compact, inexpensive, efficient and easy-to-maintain mobile system for preventing ambient release of anesthetic substances.

It is a related object of this invention to provide such a system in a form mountable to a gas cart that also supports supply cylinders containing oxygen and an anesthetic substance.

It is a further related object of this invention to provide a system as described above, operable without the need for an outside power source to induce any flows.

It is an even further related object of this invention to provide a compact, inexpensive, efficient, easy-to-maintain, cart-mounted mobile system for preventing release of anesthetic substances at selected locations, with all necessary flows being generated by pressures inherent to the gas/anesthetic system and the animal patient.

Yet another related further object of this invention is to provide a system as described hereinabove, with the option for its use in conjunction with either a system in which waste gases are exhausted directly from the system or one in which a portion of the waste gas is recycled, i.e., what is commonly known as a "rebreathing system".

These and other related objects of the present invention are accomplished by providing apparatus for scavenging an anesthetic substance from a waste gas flow leaving an anesthetic administration system, comprising means for containing a quantity of an adsorbing medium, disposed to receive a flow of waste gas from the anesthetic administration system to percolate the waste gas through the adsorbing medium for adsorption of said anesthetic substance by said adsorbing medium; and means for quickly connecting and disconnecting said adsorbing medium containing means to said anesthetic-administration system such that said flow of waste gas is caused solely by an internal pressure of the anesthetic adminstration system.

In another aspect of this invention, there is provided a system for administering a gaseous or vaporized anesthetic substance to an animal for surgical purposes, comprising a supply of oxygen, a supply of the anesthetic substance, and means for generating and delivering a controlled mixture of the anesthetic substance and oxygen to the animal; means for receiving and flowing a first waste gas exhaled by the animal, such first waste gas including any anesthetic substance exhaled by the animal; and means for scavenging said anesthetic substance from said flow of first waste gas by flowing the same through a quantity of a material selected to adsorb the anesthetic substance, said flow of first waste gas being obtained solely by the pressure at which the same is received from the animal.

DESCRIPTION OF THE PREFERRED EMBODIMENTS

Prior to surgery, the animal patient is usually given a pre-surgery injection of anesthetic. Once the animal is thus anesthetized, an endo-tracheal tube is inserted, a tube cuff thereof is sealed, and a flow of an oxygen-/anesthetic gas mixture is started. At this time, the animal is prepped by shaving and scrubbing the selected surgical body site and is thereafter moved into an operating room for surgery. During these activities, the gas connection between the animal and the typical anesthesia cart supporting the supply of oxygen and anesthetic substance is disconnected and reconnected numerous times in order to place the animal in proper surgical position.

Generating an anesthetic agent in a gaseous or vaporized form is a relatively simple process. Typically, a liquid anesthetic agent is stored in a wick-equipped reservoir through which is passed a flow of oxygen gas. The liquid anesthetic is evaporated from the wick and is mixed in with the flow of oxygen, control being exercised to achieve a desired concentration. In such systems, halothane is usually administered at a concentration in the range 0.5-1.2% and methoxyflurane at 0.4-1.0% in oxygen.

Figure 1:
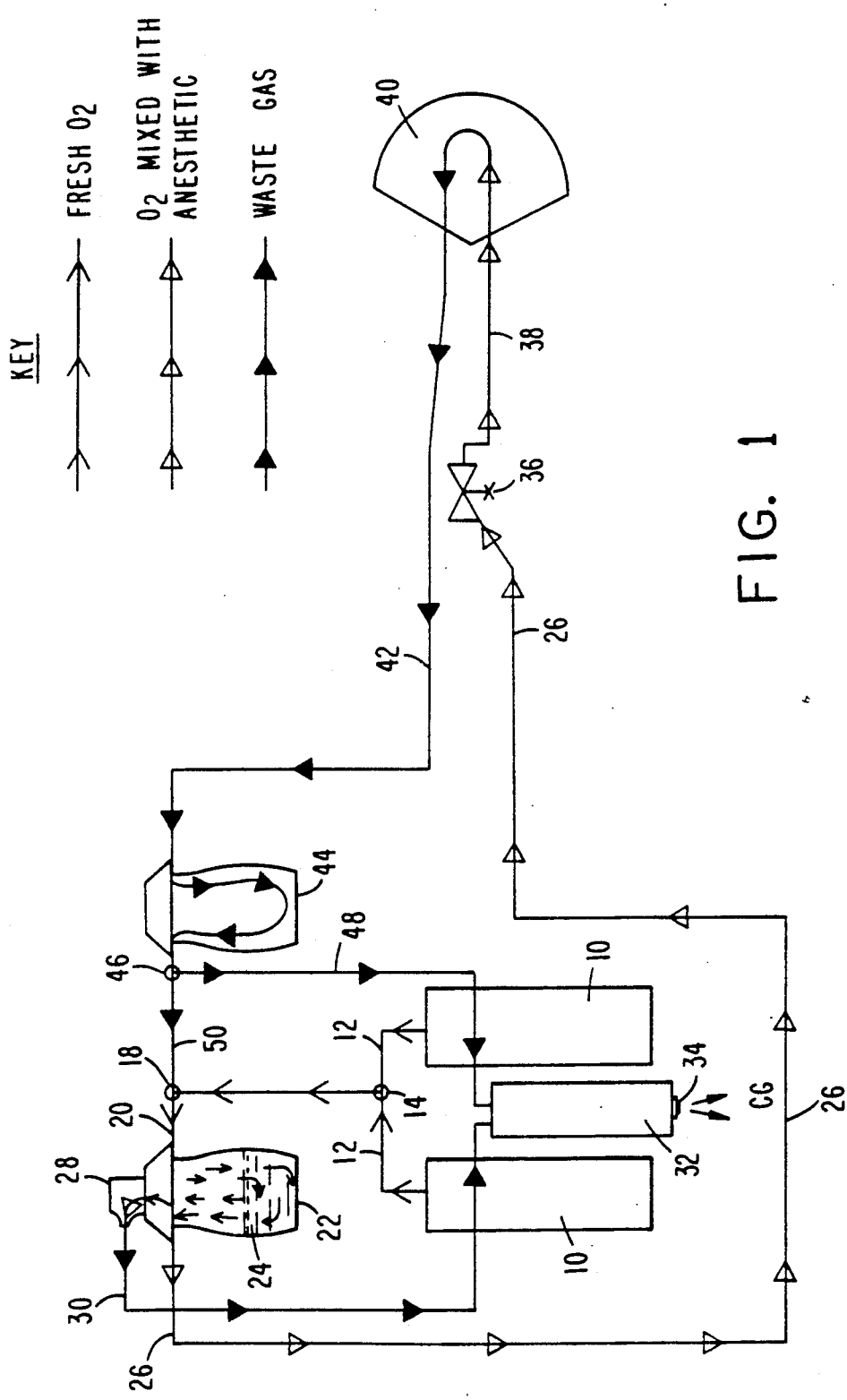
FIG. 1 is a schematic diagram illustrating various flows in an anesthetic-administration system used in conjunction with a preferred embodiment of the present invention.

Referring now to FIG. 1, which schematically illustrates a typical system of the type with which the present invention may be used, there are seen various flows of interest. It is commonplace to have two oxygen cylinders 10,10 which contain pure oxygen under high pressure. The oxygen cylinders, through control valves (not shown in FIG. 1 for simplicity), deliver gaseous oxygen to delivery lines 12,12 which are connected by a conventional junction valve 14 to a common oxygen delivery line 16. Note that this arrangement allows an operator to draw oxygen from one cylinder until it is about exhausted and then to rapidly switch over to the other cylinder while the first is being replaced.

As is indicated in the "KEY" in FIG. 1, the flow of fresh oxygen is indicated by a series of open barbed arrow heads. Thus line 16 delivers a controlled supply of pure oxygen to a dual flow control valve 18 of known design. In one operational position this valve 18 directs the incoming flow of oxygen line 16 to an intake line 20 of an oxygen-anesthetic mixing chamber 22. As mentioned earlier, this mixing chamber 22 may be of a type containing a quantity of a liquid anesthetic agent 24 (indicated generally by broken horizontal lines in FIG. 1), which is exposed through a wick or otherwise to the gas flow entering mixing chamber 22 through intake line 20. As a result, some of the liquid anesthetic agent evaporates and mixes with the oxygen, and leaves mixing chamber 22 through outflow line 26. As indicated in the "KEY" of FIG. 1, this flow of oxygen mixed with a vaporized anesthetic substance is indicated by hollow triangular arrow heads the peaks of which indicate the direction of flow.

There may be situations in which the liquid anesthetic agent 24 in mixing chamber 22 evaporates by receiving heat from the ambient atmosphere even when an oxygen flow is not being directed through chamber 22. The vaporized anesthetic thus generated is typically allowed to escape chamber 22 through a pop-off valve 28. For consistency with the earlier-discussed definition, such a flow of anesthetic, whether or not it is mixed in with any oxygen, is regarded as a "waste" gas. In most veterinary facilities, such escape of waste gas from the pop-off valve of the oxygen-anesthetic mixing chamber is routinely released within the working environment, where it may be breathed in by the surgeons and staff. The present invention is intended to remove the anesthetic substance thus flowing out from pop-off valve 28, by first receiving it in waste gas line 30. As indicated in the "KEY" of FIG. 1, such a flow of "waste gas" is indicated by solid black arrow heads.

In a system equipped with the present invention, this flow of waste gas is carried by line 30 to an anesthetic-scavenging cartridge 32 which is described more fully hereinbelow. Persons skilled in the relevant arts will appreciate that actuation of pop-off valve 28 is caused by a rise in vapor pressure within mixing chamber 22 to a predetermined level and that, therefore, such a pressure is available to drive the waste gas through an anesthetic-scavenging cartridge 32. This cartridge 32, as described more fully hereinafter, very efficiently removes the anesthetic substance by adsorbing it with a quantity of activated charcoal powder and releases any oxygen that left mixing chamber 22 with the waste gas through a clean gas outlet 34 as generally indicated by arrows "CG". Obviously, other suitable substances may be added to the activated charcoal or used in lieu thereof as most appropriate in light of the anesthetic substances used or operational circumstances.

Once the flow of oxygen is mixed in at a controlled concentration with vaporized or gaseous anesthetic substance 24, this mixture flows through line 26 to a control valve 36 with which an anesthesiologist regulates the flow to a patient-inhalation line 38. The oxygen-anesthetic mixture may be administered in any convenient form through any suitable means 40 to the animal patient. Thus element 40 may be a conventional anesthetic mask. In the alternative, for certain types of operations, this flow of oxygen-anesthetic may be administered to the patient through an endo-tracheal tube. The patient then inhales both the oxygen and the anesthetic mixed in therewith and exhales some $CO_2$, some oxygen and some anesthetic substance, as another "waste gas" breathed out through the patient-exhalation line 42. The waste gas flowing in line 42, driven by the exhalation activity of the patient and not by any motor, blower or fan, is typically passed into a $CO_2$-removing chamber 44 wherein substantially all of the $CO_2$ is removed in known manner. The remaining oxygen and anesthetic, together with any other gases exhaled by the patient, i.e, technically still a waste gas, flows from carbon dioxide-removing chamber 44 to a two-way valve 46.

This two-way valve 46 can be operated, in a first option, to simply pass through the flow of waste gas, still containing exhaled anesthetic substances, to a waste gas line 48 leading to cartridge 32 for removal of the anesthetic substance therefrom. Alternatively, in what is known as a "rebreathing system" the waste gas is directed via waste gas line 50 to valve 18. If the latter option is exercised, waste gas from line 50, which is substantially the exhaled gas from the patient with the $CO_2$ removed, is mixed with a replenishment flow of oxygen (to make up for the oxygen utilized by the patient) and is passed through intake line 20 into oxygen-anesthetic mixing chamber 32 to be recycled. If, instead, the waste gas from the $CO_2$-removing chamber 44 is directed by valve 46 to pass through waste gas line 48 into anesthetic-removing cartridge 32, the powdered activated charcoal therein adsorbs substantially all of the anesthetic substance and passes through the oxygen that was not used by the patient, together with any other exhaled gases not also scavenged out by the activated charcoal. Thus a flow of oxygen flows through cartridge 32 and is ejected from outlet valve 34 thereof as a flow of clean gas, i.e, as part of "CG" in FIG. 1.

The preceding description relates generally to the manner in which a typical system, whether utilized as a "rebreathing system" or a "pass through" system, is operated in conjunction with the present invention to remove gaseous or vaporized anesthetic substances exhaled by an animal patient or released through the pop-off valve of the oxygen-anesthetic mixing chamber 22. A detailed description is now provided of the manner of mounting a preferred embodiment of the invention to a conventional anesthetic cart, with reference to FIG. 2, and additional details are provided of the extremely simple structure of the cartridge 32.

Figure 2:
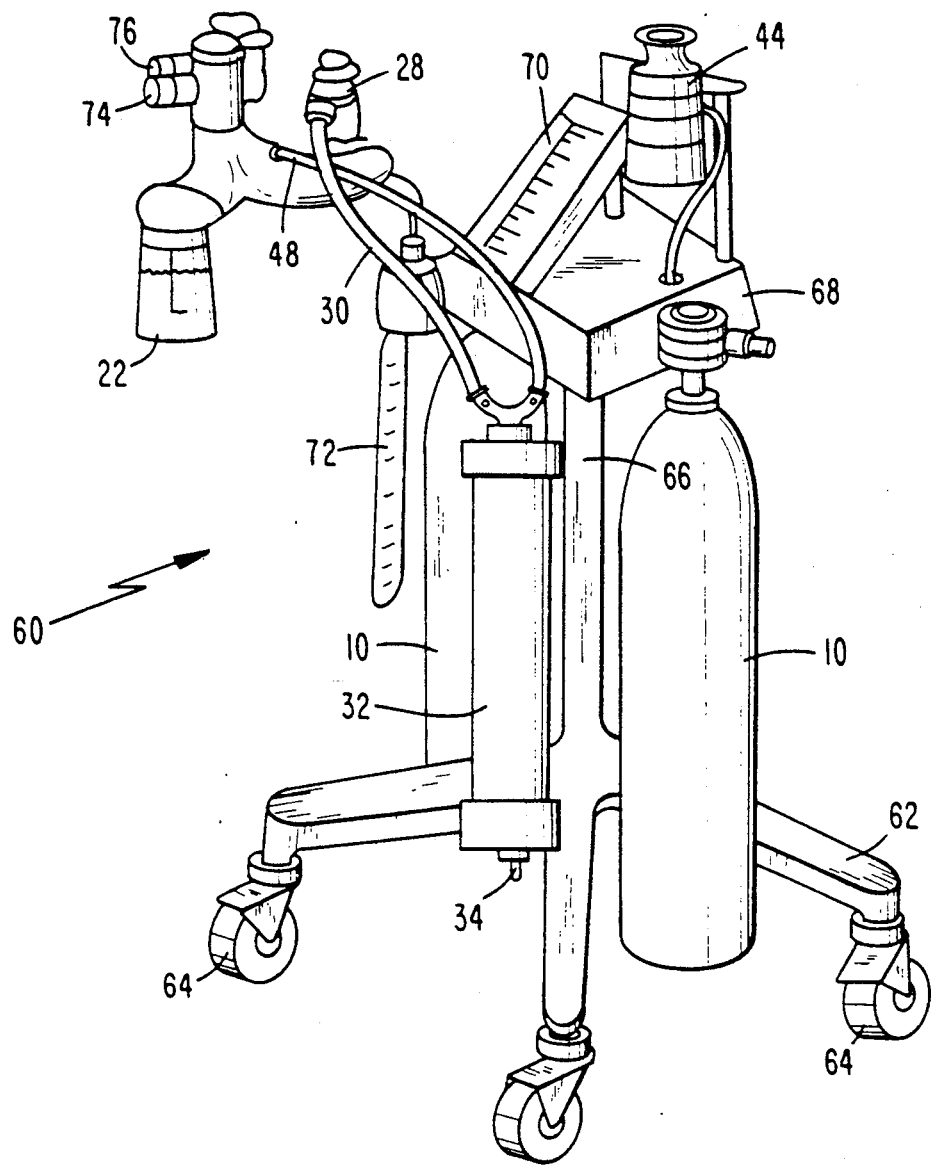
FIG. 2 is a perspective view of a portion of the anesthetic-administration system per FIG. 1, including principally an anesthetic cart and elements readily supportable thereby.

As best seen in FIG. 2, a typical anesthetic cart 60 has a plurality of support legs 62 conveniently mounted to individual castered rollers 64. Legs 62 support a substantially vertical limb 66 to which is mounted a support platform 68. Platform 68 support oxygen cylinders 10,10 in balanced manner and supports cartridge 32 with its outlet valve 34 depending therebelow. Platform 68 may also support, for example, a $CO_2$-removing chamber 44, the oxygen-anesthetic mixing chamber 32, an oxygen-anesthetic flow meter 70, and the like. Cart 60 may also be provided with a handle 72 to facilitate pushing or pulling movement of the cart. Conventional "snap-on" or "quick-release" type hose fittings 74 (for connecting to line 26 to carry oxygen-anesthetic mixture to the patient) and 76 (for connecting to line 20) may also be disposed and supported by the cart as most suitable.

Figure 3:
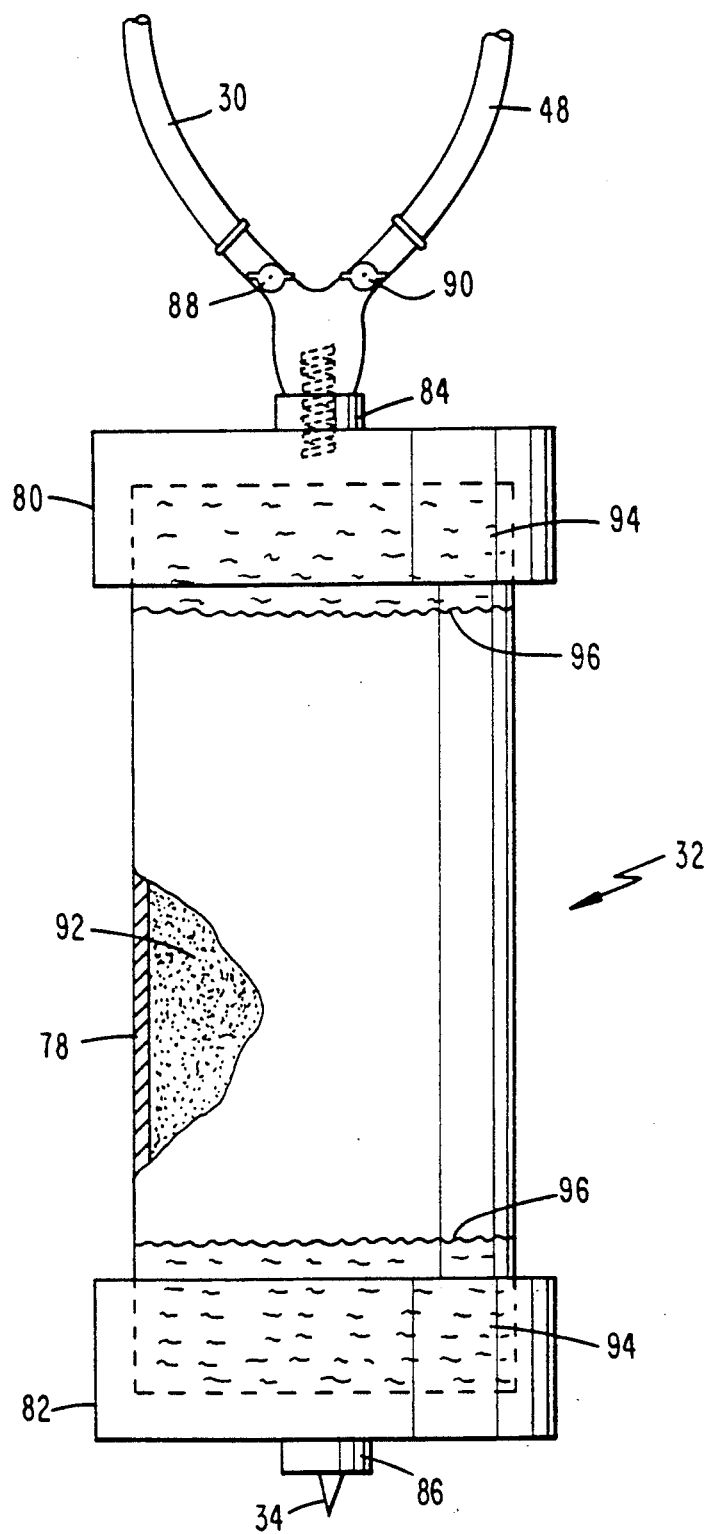
FIG. 3 is a partially-sectioned elevation view of the structure according to a preferred embodiment of this invention.

The present invention, as previously indicated, is intended to be both compact and inexpensive. The preferred embodiment of this invention, as reduced to practice, is illustrated in partially sectioned elevation view in FIG. 3. In this embodiment, the anesthetic scavenging cartridge 32 has a cylindrical body 78 which in the prototype was a 16" length of 4" diameter Schedule 40 PVC pipe of a type commercially available in most hardware stores. This cylindrical length of pipe 78 is closed at its upper end by a cap 80 and at a lower end by a similar cap 82. Caps 80 and 82 may be attached to cylindrical length 78 in any known manner, e.g., by threading or gluing thereto. Both the caps 80 and 82, in the prototype, were centrally drilled and tapped and were respectively provided with ¾" fittings 84 and 86. Upper fitting 84 was connected to a two-way garden hose adapter, the two branches of which were provided with individual shut-off valves 88 and 90 to which were connected to waste gas lines 30 and 48, respectively. Note that fitting 86 at the exit side of cartridge 32 can be readily connected to the inlet side of another similar cartridge to provide a ganged, series-connected pair of anesthetic-removing cartridges for a higher performance rating or a more thorough removal of anesthetic from the waste gas provided thereto.

Most of the volume within the cylindrical length of pipe 78 is filled with powered activated charcoal 92, e.g., of the type commercially sold for use with household aquariums, sufficient charcoal being provided to scavenge anesthetic substances for a few hours without needing a replacement yet not packed so tightly as to present a substantial flow impedance to the flow of waste gas therethrough. In the prototype model, the pressure drop through the cartridge was determined to be less than 7.5 mm Hg, a value low enough to not interfere with the function of the anesthetic system or respiratory functions of the patient animal.

The powdered activated charcoal 92 is held centrally of the length of pipe 78 by two end elements 94 in the form of disks of fiberglass filter material. Since it is desirable to utilize most of the available volume to contain loosely packed powdered activated charcoal material 92, the thickness of fiberglass filter and elements 94 needs to be only sufficient for this purpose. Thus the distance between the fiberglass-activated charcoal interface screens 96,96 should be maximized to the extent possible. In other words, the precise thickness of fiberglass end elements 94 is not critical and persons of ordinary skill in the art can be expected to select the thicknesses therefor or to use alternatives as deemed most appropriate.

Experiments with the prototype indicate that with flow rates in the range 2.0–4.0 liters per minute waste gas flow rates, with a 2.0% concentration of methoxyflurane or 1.0 concentration of halothane, with hours of desired service life, 2.5 kilograms of powdered activated charcoal would provide about 100 hours of service life. In terms of real-life surgical practice, 100 hours of service life for small veterinary clinics should provide between 9 and 12 months of active use before significant deterioration would be noticed in the ability of cartridge 32 to scavenge the anesthetic substances from the waste gas flows. Naturally, by providing the larger cartridge a service life can be commensurately extended.

When it is determined that the powdered activated charcoal 92 in a cartridge 32 has been used long enough, the cartridge can be shaken strongly to obtain further use from the same activated charcoal. The reason for this is that when the powdered activated charcoal 92 is first filled into the cartridge 32, certain flow paths become available to the waste gas flow therethrough. Adsorption of the anesthetic material occurs at the exposed surfaces of the activated charcoal particles defining such flow paths. Therefore, when the myriad of small activated charcoal particles is shaken up, new passages are defined by newly exposed surfaces of the constituent particles and, at least for a while, the ability to remove, i.e., scavenge, anesthetic substances, is restored. Eventually, the end caps may be removed, the exhausted charcoal and end filter elements 94 removed therefrom, and a fresh set of fiberglass end elements 94 provided to contain therebetween a fresh supply of activated powdered charcoal 92.

It will be immediately apparent to persons of ordinary skill in the art that metal may be used in place of the PVC material for forming cartridge 32. Also, if such cartridges are made in sufficient manufacturing volume then the economics of manufacture may justify throwing away an exhausted cartridge and replacing it with the new one, and other obvious modifications may be made to the structure described in detail herein.

Experimental studies with the prototype of the preferred embodiment of this invention indicate that the concentration of anesthetic substances in the waste gas can be reduced to less than 5% in the passage of the waste gases through powdered activated charcoal in the manner described. This 95% scavenging is believed to represent a highly efficient system. Combined with the simplicity of structure, the compactness, the low cost, and the easy maintenance of the described invention, it is believed that significant reductions in anesthetic concentrations to which veterinary surgical staff are exposed can be readily realized by this invention. Details of the study and the development of the prototype were described in an oral presentation to the American Industrial Hygiene Conference, during the Health Care Industries Session on May 25, 1989, at St. Louis, Mo. The written paper corresponding thereto has been presented for review pending publication in the American Industrial Hygiene Journal and is intended to be incorporated herein by reference especially for its detailed description of experimental results obtained in a study leading to development of this invention.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. Apparatus for scavenging an anesthetic substance from a waste gas flow leaving an anesthetic-administration system, the waste gas flow comprising at least one of a flow of unused anesthetic in gas or vapor form and anesthetic in the exhalation from a patient, comprising:
   containing means for containing a quantity of a replaceable adsorbing medium, disposed to receive a flow of waste gas from the anesthetic-administration system to percolate the waste gas through the adsorbing medium for adsorption of said anesthetic substance by said adsorbing medium, said adsorbing medium being loosely contained so as to allow shaking thereof to rearrange the same to extend its adsorbing ability; and
   means for quickly connecting and disconnecting said containing means to said anesthetic-administration system in such a manner that said waste gas flow is caused solely by an internal pressure within the anesthetic administration system.

2. Apparatus according to claim 1, further comprising:
   mobile support means for supporting said absorbing medium containing means and said connecting means in such a manner that the connecting means is readily movable to a plurality of different locations, for thereby quickly connecting the same to anesthetic-administration systems respectively located at said locations.

3. Apparatus according to claim 1, wherein:
   said adsorbing medium comprises powdered activated charcoal contained in said containing means to present an adsorbing surface for adsorbing a portion of said waste gas flow, said adsorbing surface being rearranged by shaking of said containing means.

4. Apparatus according to claim 1, wherein:
   said containing means comprises a hollow closed cylinder having an inlet end and an outlet end, the cylinder being provided with a waste gas inflow fitting at said inlet end and a scavenged gas outflow fitting at said outlet end, a quantity of powdered activated charcoal being loosely contained within the cylinder having a plurality of filter elements disposed between said inlet and outlet ends.

5. Apparatus according to claim 4, wherein:
   each of said filter elements comprises a predetermined thickness of fiberglass material and a screen layer disposed immediately adjacent to the powdered activated charcoal to retain the loosely contained powdered charcoal in a manner facilitating percolation of the waste gas therethrough, whereby adsorbing surfaces of particles of said powdered activated charcoal are rearranged and exposed for absorption of more anesthetic substances thereat upon shaking of the closed cylinder.

6. Apparatus according to claim 1, wherein:

said connecting means is connected to said anesthetic administration system to selectively receive therefrom either a flow of waste gas emitted from a source of the anesthetic substance in the anesthetic-administration system or a flow of waste gas exhaled by a patient to whom the anesthetic substance has been administered by the anesthetic-administration system.

7. Apparatus according to claim 5, wherein:

said connecting means is connected to said anesthetic administration system to selectively receive either a flow of waste gas emitted from a source of the anesthetic substance in the anesthetic-administration system or a flow of waste gas exhaled by a patient to whom the anesthetic substance has been administered by the anesthetic-administration system.

8. A system for administering a mixture of a gaseous or vaporized anesthetic substance and oxygen to an animal for surgical purposes the animal inhaling the mixture and exhaling at least one waste gas, comprising:

a supply of oxygen, a supply of the anesthetic substance, and means for generating and delivering a controlled mixture of the anesthetic substance and oxygen to the animal;

means for receiving and conveying a first waste gas flow exhaled by the animal, such first waste gas flow including any anesthetic substance exhaled by the animal; and means for scavenging said exhaled anesthetic substance from said first waste gas flow, by flowing the same through a quantity of an adsorption material selected to adsorb the exhaled anesthetic substance, said first waste gas flow being obtained solely by the pressure at which the same is received from the animal, wherein said adsorption material comprises a quantity of particles held between end elements enabling gas flow therethrough, said particles being loosely packed to allow redistribution thereof by shaking to thereby expose other adsorbing surfaces of said particles to adsorb the anesthetic substance thereat.

9. The system according to claim 8, further comprising:

mobile support means for movably supporting at least said oxygen supply, said anesthetic substance supply an said scavenging means to facilitate convenient movement thereof.

10. The system according to claim 9, further comprising:

means for receiving and flowing a second waste gas flow comprising a vented mixture of oxygen and anesthetic substance released solely from said mixture generating and delivering means to said scavenging means for scavenging of the vented anesthetic substance therefrom.

11. The system according to claim 10, further comprising:

means for scavenging carbon dioxide from said first waste gas flow.

12. Apparatus according to claim 1, wherein:

said connecting means is connected to said apparatus for selective use with a rebreathing or a non-rebreathing anesthetic-administration system.

13. The system according to claim 8, further comprising:

means for flowing said first waste gas flow to enable selective operation of the system as either a rebreathing or a non-rebreathing system.

* * * * *